(12) United States Patent
Glibert

(10) Patent No.: US 11,246,779 B2
(45) Date of Patent: Feb. 15, 2022

(54) MANUAL ASSISTANCE TRANSFER BELT UTILIZING INDIVIDUAL THIGH STRAPS

(71) Applicant: Ola Lysenstoen, Newbury Park, CA (US)

(72) Inventor: Christian Glibert, Oxnard, CA (US)

(73) Assignee: Ola Lysenstoen, Newbury Park, CA (US)

( * ) Notice: Subject to any disclaimer, the term of this patent is extended or adjusted under 35 U.S.C. 154(b) by 723 days.

(21) Appl. No.: 15/671,069

(22) Filed: Aug. 7, 2017

(65) Prior Publication Data

US 2018/0036190 A1 Feb. 8, 2018

Related U.S. Application Data

(60) Provisional application No. 62/371,211, filed on Aug. 5, 2016.

(51) Int. Cl.
| | | |
|---|---|---|
| *A61F 5/37* | (2006.01) | |
| *A61G 7/10* | (2006.01) | |
| *A61F 5/03* | (2006.01) | |
| *A62B 35/00* | (2006.01) | |

(52) U.S. Cl.
CPC ............ *A61G 7/1023* (2013.01); *A61F 5/03* (2013.01); *A61F 5/37* (2013.01); *A61G 7/1015* (2013.01); *A61G 7/1051* (2013.01); *A61G 2200/34* (2013.01); *A61G 2200/36* (2013.01); *A62B 35/0025* (2013.01)

(58) Field of Classification Search
CPC .. A61G 7/1015; A61G 7/1023; A61G 7/1051; A61G 2200/34; A61G 2200/36; A61F 5/03; A61F 5/37; A62B 35/0025
See application file for complete search history.

(56) References Cited

U.S. PATENT DOCUMENTS

| | | | |
|---|---|---|---|
| 1,035,642 A | 8/1912 | Rosse | |
| 3,234,568 A * | 2/1966 | Fischer | ............... A61G 7/1061 5/89.1 |
| 4,076,101 A | 2/1978 | Himmelrich | |
| 4,221,011 A * | 9/1980 | Flinchbaugh | ............ A61G 7/10 5/89.1 |
| 4,739,526 A * | 4/1988 | Hollick | ............... A61G 7/1015 5/83.1 |

(Continued)

FOREIGN PATENT DOCUMENTS

EP 1 344 552 A1 * 3/2003

OTHER PUBLICATIONS

English translation of EP 1 344 552 A1 (Year: 2003).*

*Primary Examiner* — Camtu T Nguyen
(74) *Attorney, Agent, or Firm* — Tope-McKay & Associates

(57) ABSTRACT

Described is a transfer belt for assisting transportation of an individual. The transfer belt includes a waist band, a pair of thigh bands, each thigh band configured to be secured around a leg of the individual; and a pair of interconnecting straps, each interconnecting strap connecting a thigh band with the waist band. A bridge strap connects the pair of thigh bands to one another to enhance stability of the individual during transportation. The transfer belt supports the patient's center of gravity, in both a seated or standing position, to allow for a transfer from a seated position to a standing position without adjusting the device.

17 Claims, 16 Drawing Sheets

(56) References Cited

U.S. PATENT DOCUMENTS

| | | | |
|---|---|---|---|
| D337,975 S * | 8/1993 | Keller | D12/128 |
| 5,388,551 A | 2/1995 | Martusciello | |
| 5,814,001 A * | 9/1998 | Schwenn | A61F 5/0193 |
| | | | 602/23 |
| 6,050,364 A | 4/2000 | Popall et al. | |
| 6,073,280 A | 6/2000 | Farnum | |
| 6,122,778 A | 9/2000 | Cohen | |
| 6,189,651 B1 | 2/2001 | Sadeck | |
| 6,311,346 B1 | 11/2001 | Goldman | |
| 6,715,167 B2 * | 4/2004 | Wake | A61G 7/1023 |
| | | | 5/81.1 T |
| 6,883,190 B2 * | 4/2005 | Carbonneau | A61G 7/10 |
| | | | 5/89.1 |
| 7,341,025 B1 | 3/2008 | Streeter et al. | |
| 7,624,458 B2 * | 12/2009 | Felling | A61G 7/1023 |
| | | | 294/140 |
| 7,627,912 B1 * | 12/2009 | McKinney | A61G 7/1011 |
| | | | 5/81.1 R |
| 8,235,173 B2 | 8/2012 | Kopp | |
| 8,250,685 B1 | 8/2012 | Kocet | |
| 8,281,430 B1 | 10/2012 | Hough et al. | |
| 8,321,972 B1 | 12/2012 | Vetter | |
| 9,687,033 B2 * | 6/2017 | Lillie | A41D 1/06 |
| 2003/0140414 A1 | 7/2003 | Wake | |
| 2004/0025250 A1 | 2/2004 | Bezalel | |
| 2007/0272484 A1 * | 11/2007 | Helms | A62B 35/0018 |
| | | | 182/3 |
| 2008/0189853 A1 | 8/2008 | Felling | |

* cited by examiner

MANUAL ASSISTANCE TRANSFER BELT UTILIZING INDIVIDUAL THIGH STRAPS

CROSS-REFERENCE TO RELATED APPLICATIONS

This is a Non-Provisional Patent Application of U.S. Provisional Application No. 62/371,211, filed on Aug. 5, 2016, entitled, "Manual Assistance Transfer Belt Utilizing Individual Thigh Straps," the entirety of which are hereby incorporated by reference.

BACKGROUND OF INVENTION

(1) Field of Invention

The present invention relates to patient lift and transfer devices, specifically manual, portable slings, which assist in the transfer of persons who have restricted or limited mobility.

(2) Description of Related Art

In today's world, there are many patients who have restricted or limited mobility issues that require assistance transitioning from one area to another. "Patient" refers to any person, regardless of age, sex, health condition, physical impairment or disability, who requires, even if only occasionally, assistance with being moved. Hospitals, nursing facilities, school staff, emergency medical technician (EMT) personnel, caregivers, and family members who work closely with limited mobility patients must constantly assist them as they transition about their daily lives. Patients may be moved or repositioned within their beds to help prevent pressure sores, moved to assist with activities of daily living such as toileting and bathing, and moved to or from a chair, bed, wheelchair, stander or vehicle. Changing or alternating a patient's positions can be a safety risk for both the caregiver and the patient being transferred utmost care must be taken. The occasionally used practices of gripping a patient's pants or limbs are a major safety risk for the patient. Additionally, grabbing and pulling on a patient's arms or legs, especially if the patient has decreased tone, can cause irreversible damage to the patient. Unsafe transfers may cause damage to the patient, including but not limited to cuts or bruising of the skin, shoulder or neck injuries, or breathing difficulties. The most common injuries to caregivers are injuries to the shoulders and lower back. Caregivers must be able to safely and efficiently transfer patients in an effective and standardized manner.

Currently, there are a variety of methods used to move or transfer patients, but they may not be suitable in many situations. Many hydraulic lifts are too complicated, cumbersome, or expensive to be used in some settings. Additionally, these lifts are difficult to position and ma involve the patient swaying back and forth, causing physical and emotional discomfort to the patient. There are many patents on the market that are designed to lift via hydraulic such as U.S. Pat. No. 5,153,953. These lifts typically attach to a bar and do not utilize manual gripping handles. Additionally, many patents involve the patient to be suspended in the air, frequently resulting in a swaying motion. A manual assistance transfer belt utilizing thigh straps can be much safer, effective, and efficient in a variety of locations.

Frequently, maximal assistance or dependent transfers must be completed in small spaces over a short period of time. The best manual practice for these transfers involves at least two well-trained persons, working in unison. Without proper training, authorized procedures and equipment, personnel may cause harm to patients by lifting them up by their arms, grabbing the patients' clothing, compressing the patients' brachial plexus by lifting underneath the armpit, or failing to support the patients' trunk and/or center of gravity.

There are many shortcomings of the prior art of transfer assistance devices. Although the transfer belt described in U.S. Pat. No. 6,311,346 (hereinafter referred to as the '346 patent) is simple to use, it does not fully secure the patient during a transfer. It frequently slides up the patient's abdomen to his/her chest. Additionally, it is not designed for any lifting of the patient, but, rather, one in assisting with movement. The "Rescue and Invalid Support Belt" disclosed in U.S. Pat. No. 6,073,280 (hereinafter referred to as the '280 patent) secures the patient more firmly than the transfer belt of the '346 patent, but is still not designed for upward lifting forces, as it will continue to slide up the patient's chest. Additionally, it does nothing to support the patient's legs during any transfer.

Furthermore, the Lift Vest described in U.S. Pat. No. 6,122,778 (hereinafter referred to as the '778 patent) is designed to help assist a patient during a transfer, but not to lift the patient off the ground. Again, it does not support the legs in any way and is primarily designed to be used by one person. The device disclosed in U.S. Pat. No. 6,715,167 is designed to only transfer a patient from one seated position to another seated position and does not allow for a transition to a standing position or vice versa. Additionally, it only utilizes one strap for the patient's legs, which would make it difficult to position and get beneath the patient's legs, along with decreased feelings of security for the patient and cannot be used to support the patient in a standing position.

U.S. Pat. No. 6,276,006 (hereinafter referred to as the '006 patent) is designed specifically for airline passengers and transfers only from one seated position to another. U.S. application Ser. No. 12/333,198 does not secure around the patient's thighs or support the legs in any way during a transfer. It also does nothing to support the upper trunk of a patient during a transfer. Moreover, U.S. Pat. No. 1,035,642A would be very difficult to position underneath a patient who is already in a seated position. Additionally, it can only be utilized to transfer from one seated position to another.

As described above, there are numerous patents that involve slipping a piece of fabric underneath the patient and lifting them up from their buttocks, but do not support the trunk or each leg individually. Not only would these products be very difficult to get underneath the patient when donning but would also be difficult to remove without shearing forces on the patient. None of the aforementioned devices utilize a system that supports the patient's center of gravity, in both a seated or standing position, to allow for a transfer from a seated position to a standing position without adjusting the device. Lastly, none of the previous art utilizes individual thigh bands along with a waist band for transfers.

Thus, a continuing need exists for better, safer solutions in transferring a patient for the safety and well-being of both the patient and the caregiver.

SUMMARY OF THE INVENTION

The present invention relates to patient lift and transfer devices, specifically manual, portable slings, which assist in the transfer of persons who have restricted or limited mobility. The transfer belt for assisting in transporting an individual comprises a waist band for securing around the waist of the individual and a pair of thigh bands, each thigh band configured to be secured around a leg of the individual. A pair of interconnecting straps connects a thigh band with the waist band, such that when the transfer belt is worn by the individual, one of the pair of interconnecting straps is positioned between the waist band and one of the pair of thigh bands along a first hip area of the individual, and the other of the pair of straps is positioned between the waist band and the other of the pair of thigh bands along a second hip area of the individual. A bridge strap connects the pair of thigh bands to one another.

In another aspect, at least one waist handle is connected with the waist band for assisting in lifting the individual.

In another aspect, at least one thigh handle is connected with each of the pair of thigh bands for assisting in lifting the individual.

In another aspect, the at least one waist handle and the at least one thigh handle are formed to be connectable with a mechanical lift.

In another aspect, the at least one waist handle is formed to be connectable with a walking assistance device.

In another aspect, the transfer belt further comprises a pair of removable supporting shoulder straps formed to be connectable with at least one of a waist handle and a thigh handle, wherein each removable supporting shoulder strap is wearable by a caretaker for transporting the individual.

In another aspect, each thigh band comprises a set of interlocking handles.

In another aspect, each of the pair of interconnecting straps is adjustable.

In another aspect, the individual wearing the transfer belt can be transferred to and from a seated position, a standing position, or a lying position without adjustments to the transfer belt.

In another aspect, a connecting strap connects the pair of removable supporting shoulder straps, such that if the pair of shoulder straps are worn by the caregivers, the connecting strap is positioned at an upper back of the individual to provide additional support to an upper torso and head of the individual.

The invention further comprises a method for forming a transfer belt for assisting in transporting an individual. The method comprises acts of forming a waist band for securing around the waist of the individual; forming a pair of thigh bands, each thigh band formed to be secured around a leg of the individual; and forming a pair of interconnecting straps, each interconnecting strap formed to connect a single thigh band with the waist band. When the transfer belt is worn by the individual, one of the pair of interconnecting straps is positioned between the waist band and one of the pair of thigh bands along a first hip area of the individual, and the other of the pair of straps is positioned between the waist band and the other of the pair of thigh bands along a second hip area of the individual. A bridge strap is formed for connecting the pair of thigh bands to one another.

In another aspect, the method comprises an act of forming at least one thigh handle connected with each of the pair of thigh bands for assisting in lifting the individual.

In another aspect, the method further comprises an act of forming a pair of removable supporting shoulder straps connectable with at least one of a waist handle and a thigh handle, wherein each removable supporting shoulder strap is wearable by a caretaker for transporting the individual.

In another aspect, the method further comprises an act of forming a set of interlocking handles connected with each thigh band.

In another aspect, the method further comprises an act of forming a connecting strap connecting the pair of removable supporting shoulder straps, such that if the pair of shoulder straps are worn by the caregivers, the connecting strap is positioned at an upper back of the individual to provide additional support to an upper torso and head of the individual.

BRIEF DESCRIPTION OF THE DRAWINGS

The objects, features and advantages of the present invention will, be apparent from the following detailed descriptions of the various aspects of the invention in conjunction with reference to the following drawings, where.

DETAILED DESCRIPTION

Figure 1:
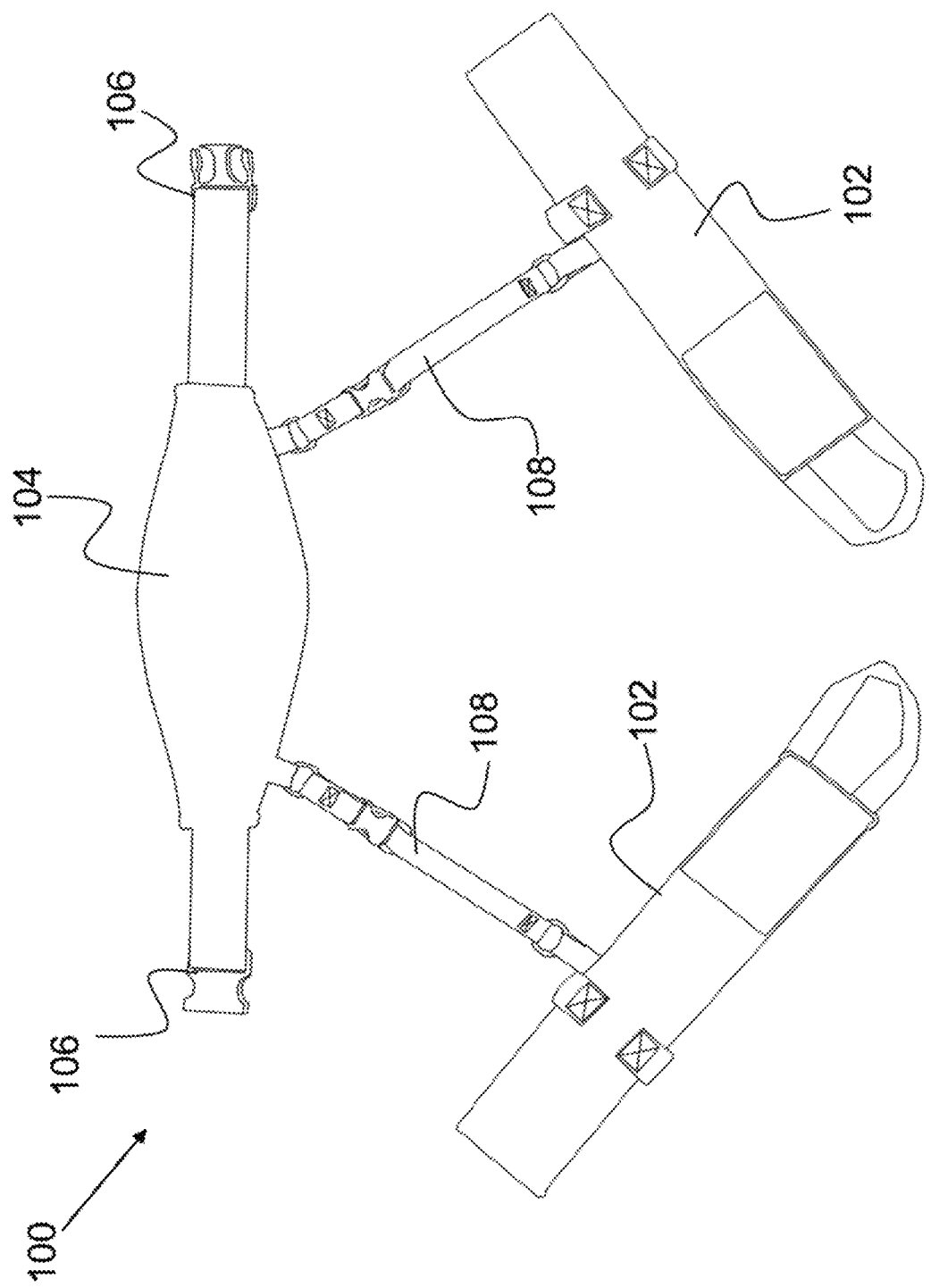
FIG. 1 is a top-view illustration of the thigh bands and waist band lying open according to some embodiments of the present disclosure.

The following description is presented to enable one of ordinary skill in the art to make and use the invention and to incorporate it in the context of particular applications. Various modifications, as well as a variety of uses, in different applications will be readily apparent to those skilled in the art, and the general principles defined herein may be applied to a wide range of embodiments. Thus, the present invention is not intended to be limited to the embodiments presented, but is to be accorded with the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter-clockwise have been used for convenience purposes only and are not intended to imply any particular fixed direction. Instead, they are used to reflect relative locations and/or directions between various portions of an object. As such, as the present invention is changed, the above labels may change their orientation.

(I) Specific Details of the Invention

The manual assistance transfer belt with adjustable thigh straps according to embodiments of the present disclosure is a manual transfer device that utilizes individual thigh straps, a chest strap, and handles for the use of assisting persons from one area to another. The development of a transfer belt utilizing individual thigh straps, as described herein, allows two trained caregivers, using good body mechanics, to move or transport a patient in a variety of settings, with minimal risk to the patient and caregivers. This compact manual assistance design, which includes a chest/waist belt, individual thigh straps and adjustable handles and straps for patient comfort and caregiver control, provides a user-friendly alternative to the variety of transfer methods that are currently being utilized. It also allows patients to be transferred to and from a variety of positions such as supine, standing, and seated, which is not typical of manual transfer devices on the market today. The apparatus is simple to understand, quick to don, comfortable for the patient, is easy to use in small or crowded spaces, and made of materials that are easily cleaned and sanitized.

Accordingly, several advantages of one or more aspects of the invention are as follows: to provide a safe and convenient way to move or transfer patients from one area to another; to provide a standardized approach to a manual assistance transfer; provision of adjustable handles to grip during transfers; device is simple to don and take off; device is easy to utilize in small/tight spaces; device is easily compactible to be carried/transported conveniently; fabric and materials are easily cleaned, sanitized and stored, device can be easily placed on the patient while standing, sitting or lying down or utilizing a wheelchair/stander/gait trainer; parallel bars, walker, chair, mat table, or vehicle; device is simple to use/understand, device fits safely and adjusts securely; device is easily adjustable to a variety of patient sizes; and device supports a patient's trunk and legs during transfer. Other advantages of one or more aspects will be apparent from a consideration of the drawings and ensuing description.

Referring to the drawings, FIG. 1 is a top-view illustration of the transfer belt 100 described herein, shown with thigh bands 102 and waist band 104 lying open. The transfer belt 100 further comprises adjustable connection straps 106 for fitting around the waist of the person. As a non-limiting example, and as shown in FIG. 1, the connection straps 106 may connect via a clip engagement. As depicted, the transfer belt 100 comprises a pair of adjustable straps 108 connecting the waist band 104 with the thigh bands 102.

Figure 2:
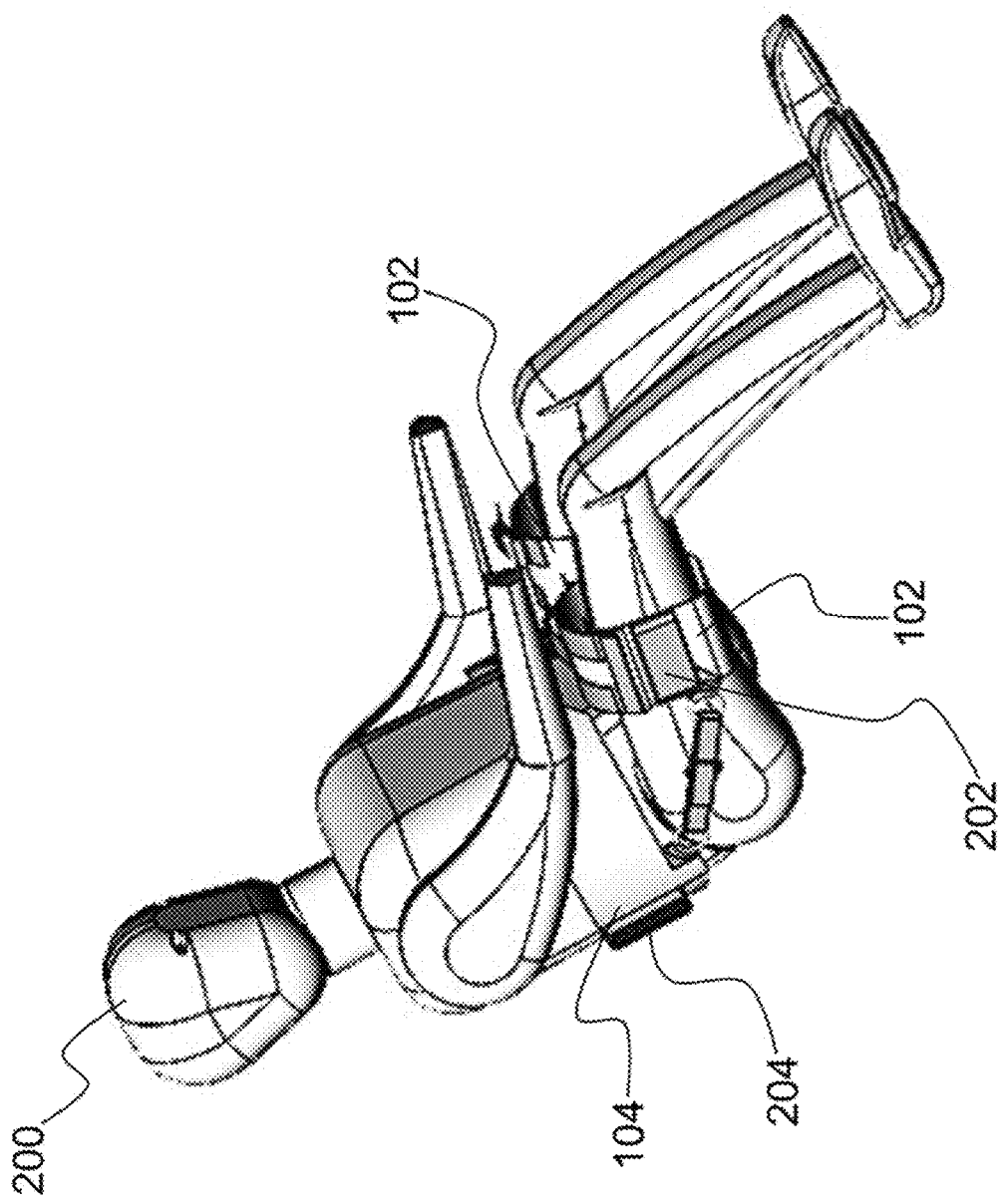
FIG. 2 is a side, perspective-view illustration of a person positioned as he would be during a transfer according to some embodiments of the present disclosure.

FIG. 2 depicts a person/patient 200 positioned as he would be during a transfer. Individual thigh bands 102 and waist band 104 are shown. The transfer belt 100 allows for an even distribution of the person's 200 center of gravity. For instance, if the posterior of the person 200 is the center of gravity, leverage on either side of that point portion of the body above the waist and portion of the body below the waist) provides stability. Furthermore, as shown in FIG. 2, the transfer belt 100 includes adjustable lift handles on the thigh bands 202 and waist band 204.

Figure 3:
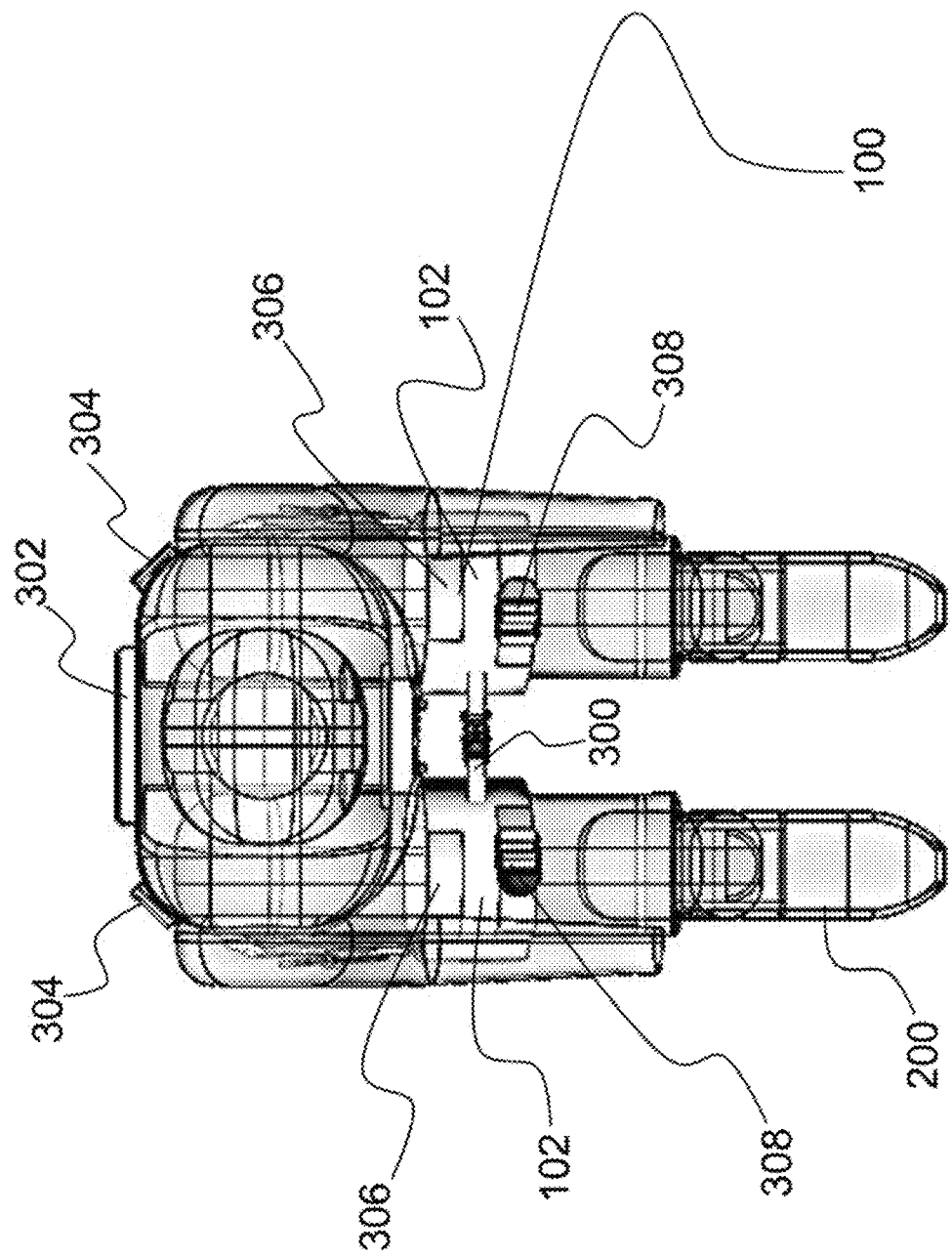
FIG. 3 is a top-view illustration of final positioning of the person in the transport belt ready for transfer according to some embodiments of the present disclosure.

FIG. 3 shows the final positioning of the person 200 in the transfer belt 100 ready for transfer, as viewed from above. In one embodiment, the transfer belt 100 comprises a bridge strap 300 with an adjustable buckle and strap connecting the two individual thigh bands 102. The bridge strap 300 acts to prevent the person's legs from separating during lifting and/or transport. The bridge strap 300 aids in safety as well as allowing the patient to feel more secure due to limited relative movement of his/her thighs.

A horizontal rear waist band lift handle 302 on the posterior aspect of the waist band 104 is illustrated with waist band lift handles 304 shown on either side. Additionally, the transfer belt 100 includes a set of interlocking handles 306 (depicted in FIG. 16) and adjustment buckle and strap 308 on each individual thigh band. The adjustable leg band lock is an adjustable handle strap comprising two handles. When gripping the handles 306 for lifting a person 200, it is important to grip both handles 306 at the same time. Each thigh band 102 has a Velcro attachment (or similar connection mechanism) to secure each thigh band 102 around each thigh of the person 200. The adjustable handle strap is such that both handles carry weight. Since the two handles coupled together via each thigh band 102 encircle each thigh, it is a very secure manner in which to carry the weight of the person 200.

Figure 4:
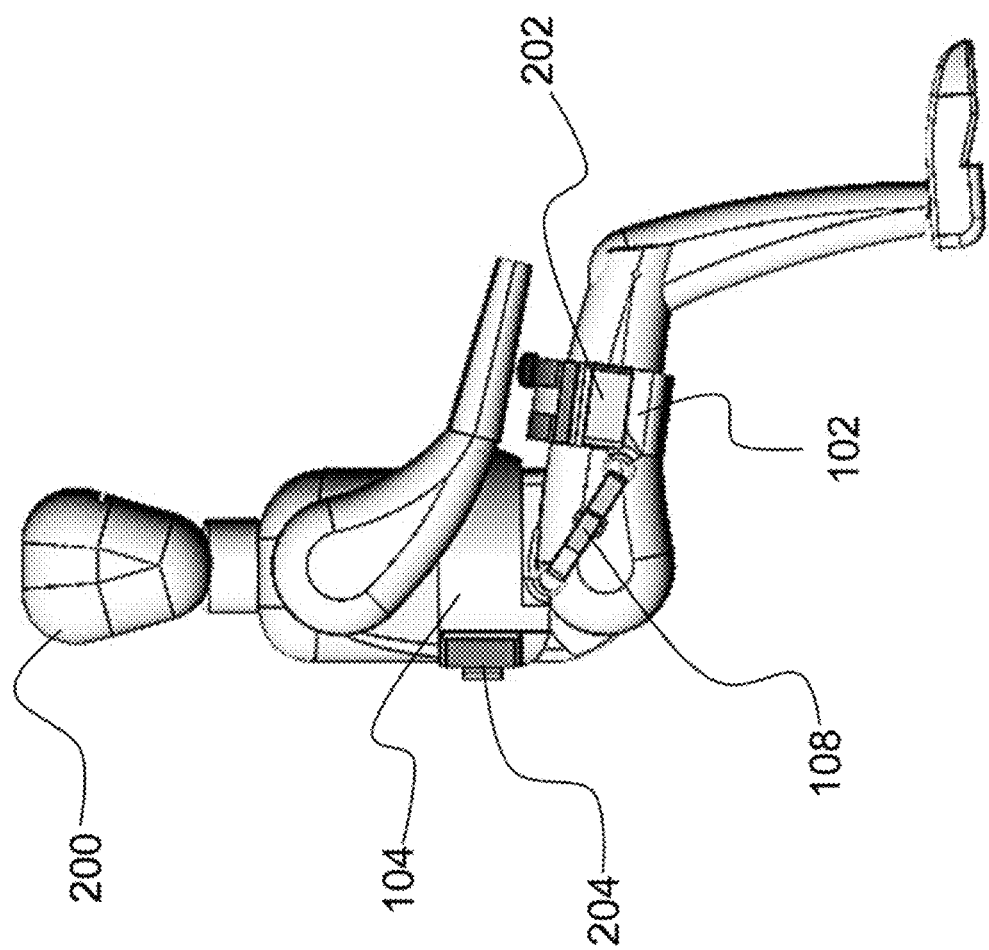
FIG. 4 is a side-view illustration of the thigh bands and waist band with a person in a seated position according to some embodiments of the present disclosure.

FIG. 4, illustrates the thigh bands 102 and waist band 104 with a person 200 in a seated position with an adjustable interconnection strap 108 with buckle connecting individual adjustable thigh bands 102 to waist band 104 and lift handles on the thigh bands 202 and waist belt 204.

Figure 5:
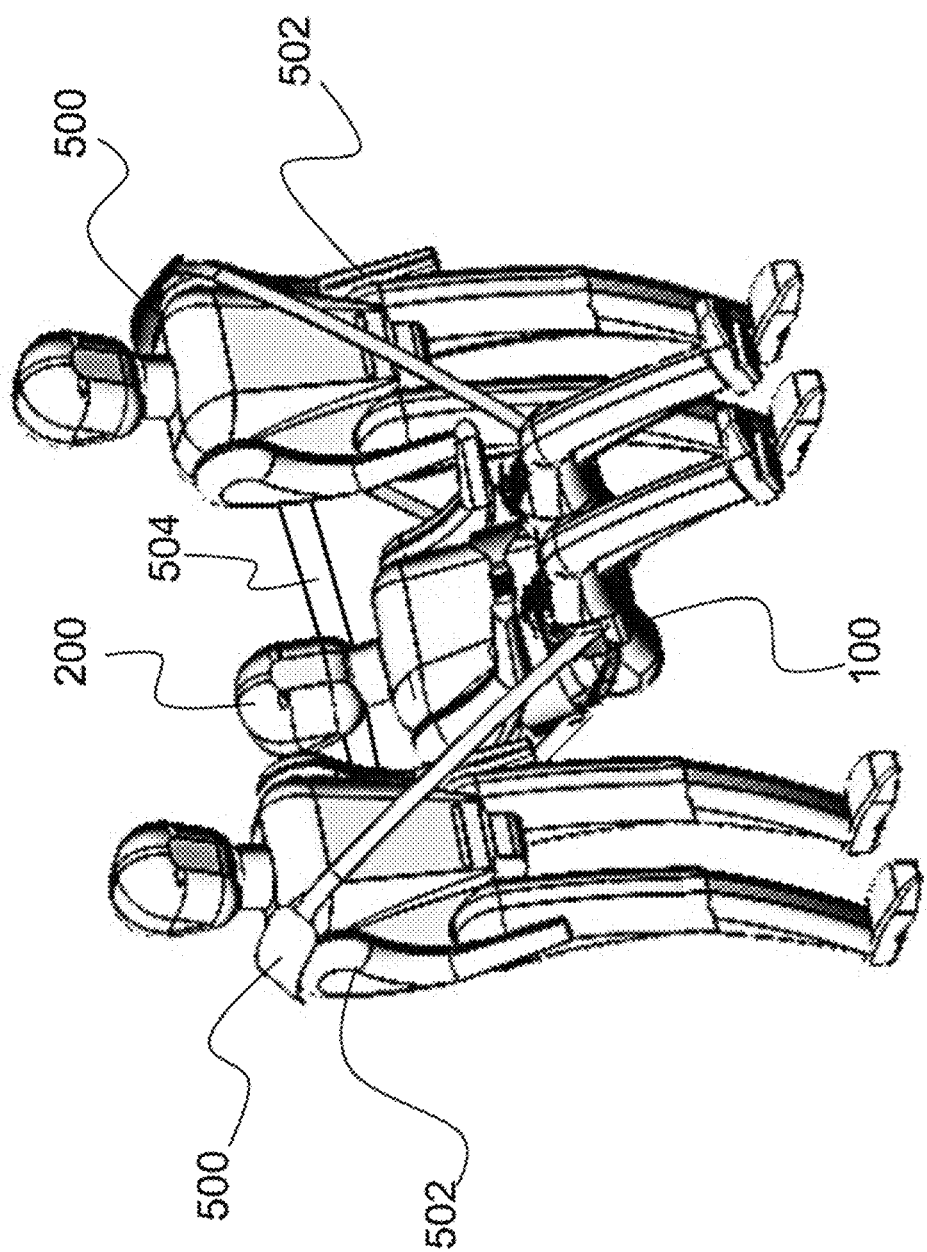
FIG. 5 is a front, perspective-view illustration of caregivers transferring a person using a right side-left side technique according to some embodiments of the present disclosure.
Figure 9:
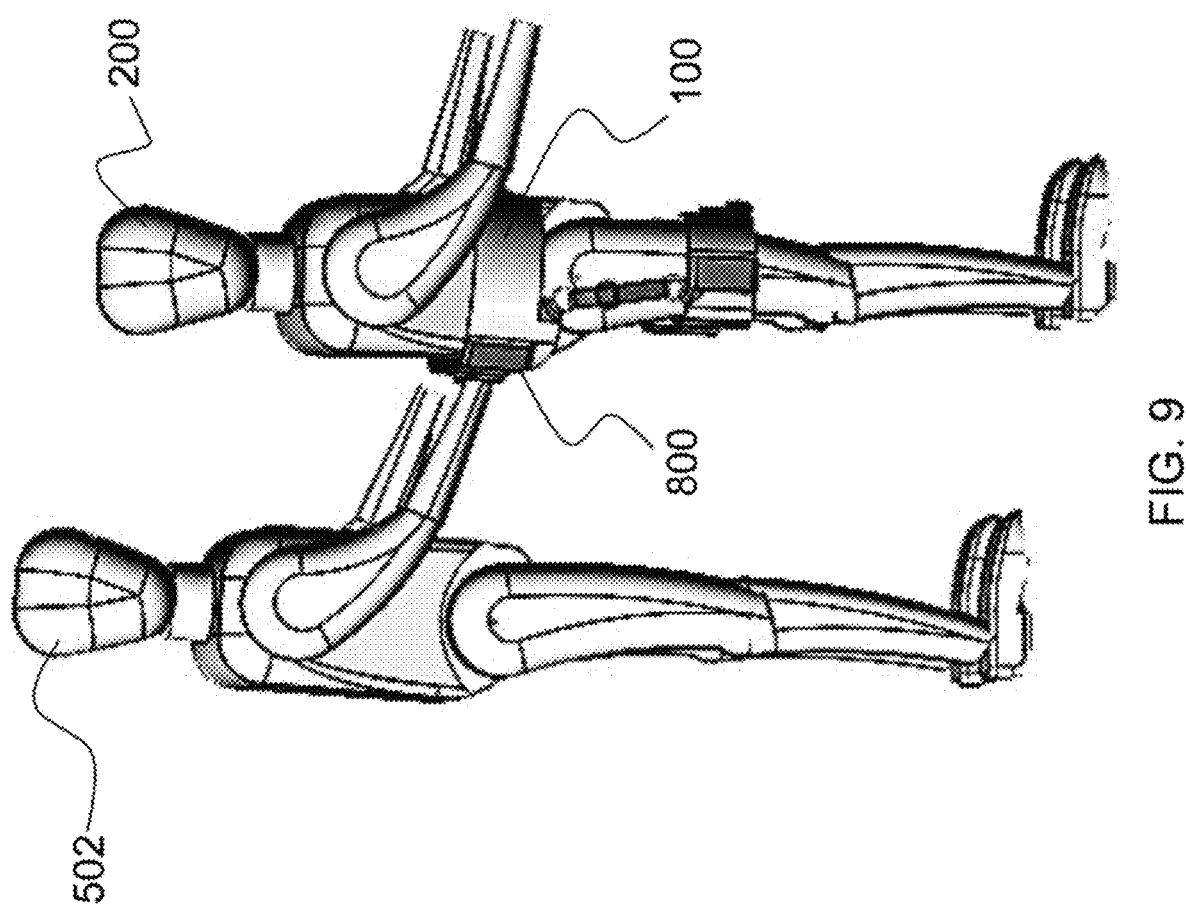
FIG. 9 is a side-view illustration of a caregiver assisting a person in a standing position according to some embodiments of the present disclosure.
Figure 10:
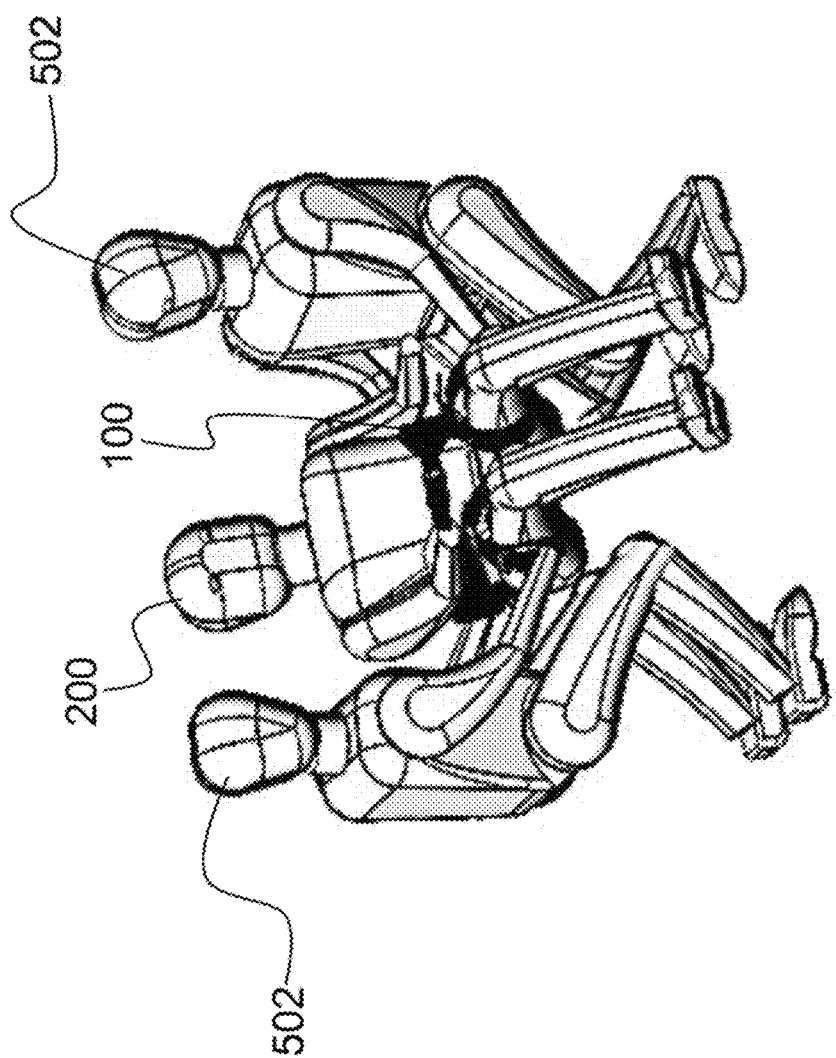
FIG. 10 is a front, perspective-view illustration of the transfer belt being used by two caregivers to transfer a person a long distance according to some embodiments of the present disclosure.

FIG. 5 shows the transfer belt 100 being used to transfer a person 200 long distances. Shoulder straps 500 are removably connected to the waist and/or thigh handles of the transfer belt 100 for transport. As shown in FIG. 5, each shoulder strap 500 is positioned over a shoulder of a caregiver 502 as an emergency long distance carry system. The shoulder straps 500 make it easier for caregivers 502 to transport the patient/person 200 over a long distance compared to grasping the waist and/or thigh handles (as shown in FIGS. 9 and 10). Furthermore, the shoulder straps 500 can further include at least one strap (or band) 504 that connects the pair of shoulder straps 500. When properly worn by the caregivers 502, the strap 504 is positioned at the upper back of the person 200 to provide additional support to the incapacitated person's 200 upper torso and head during emergency transport. This type of configuration would be extremely beneficial in search and rescue and/or military scenarios where a stretcher would be too cumbersome. The described transfer belt 100 and shoulder straps 500 provide a lightweight and portable, yet also safe and stable, solution to emergency transport of incapacitated individuals.

Figure 6:
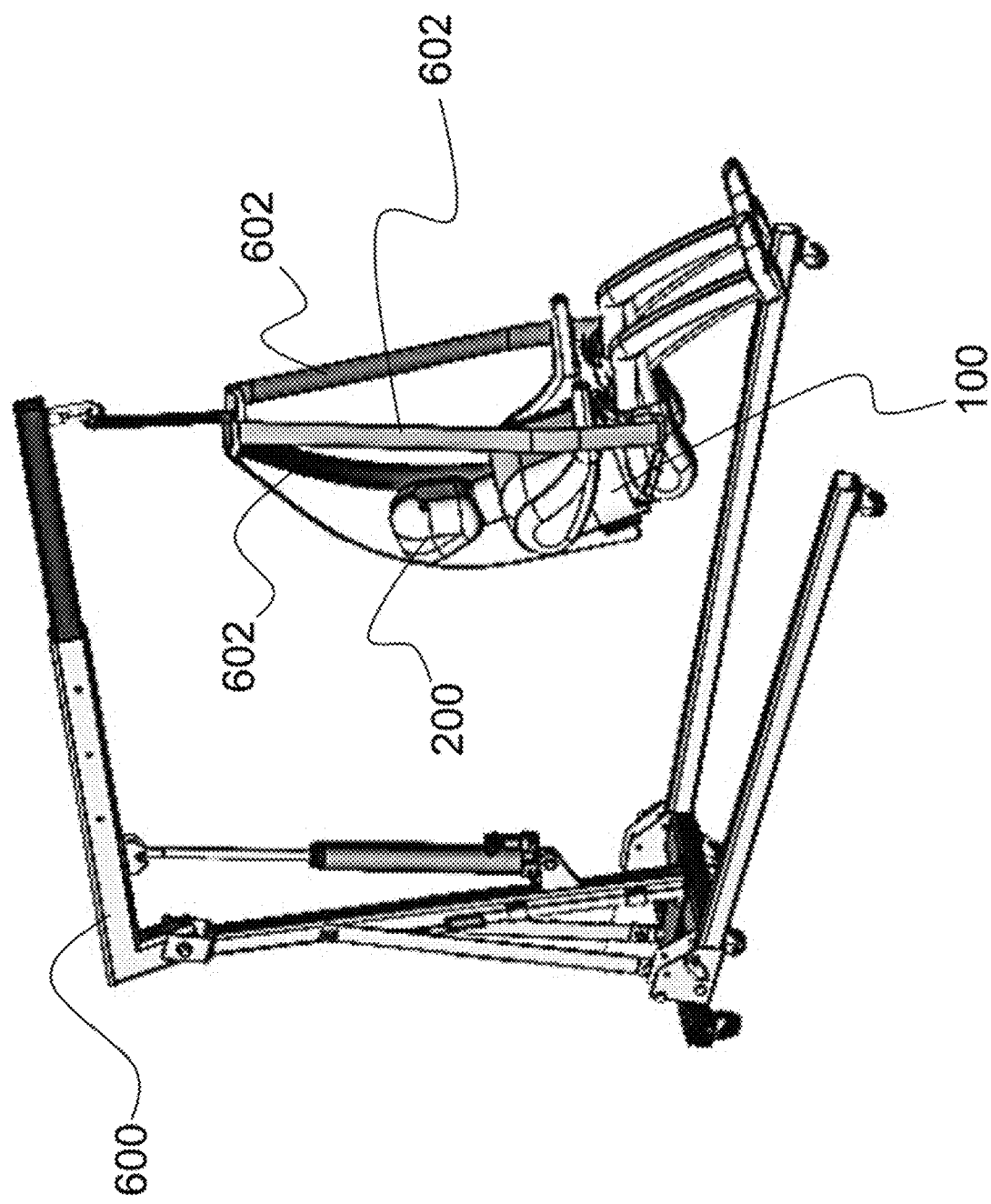
FIG. 6 is a side, perspective-view illustration of a person utilizing the transfer belt to be transferred with a mechanical lift according to some embodiments of the present disclosure.
Figure 7:
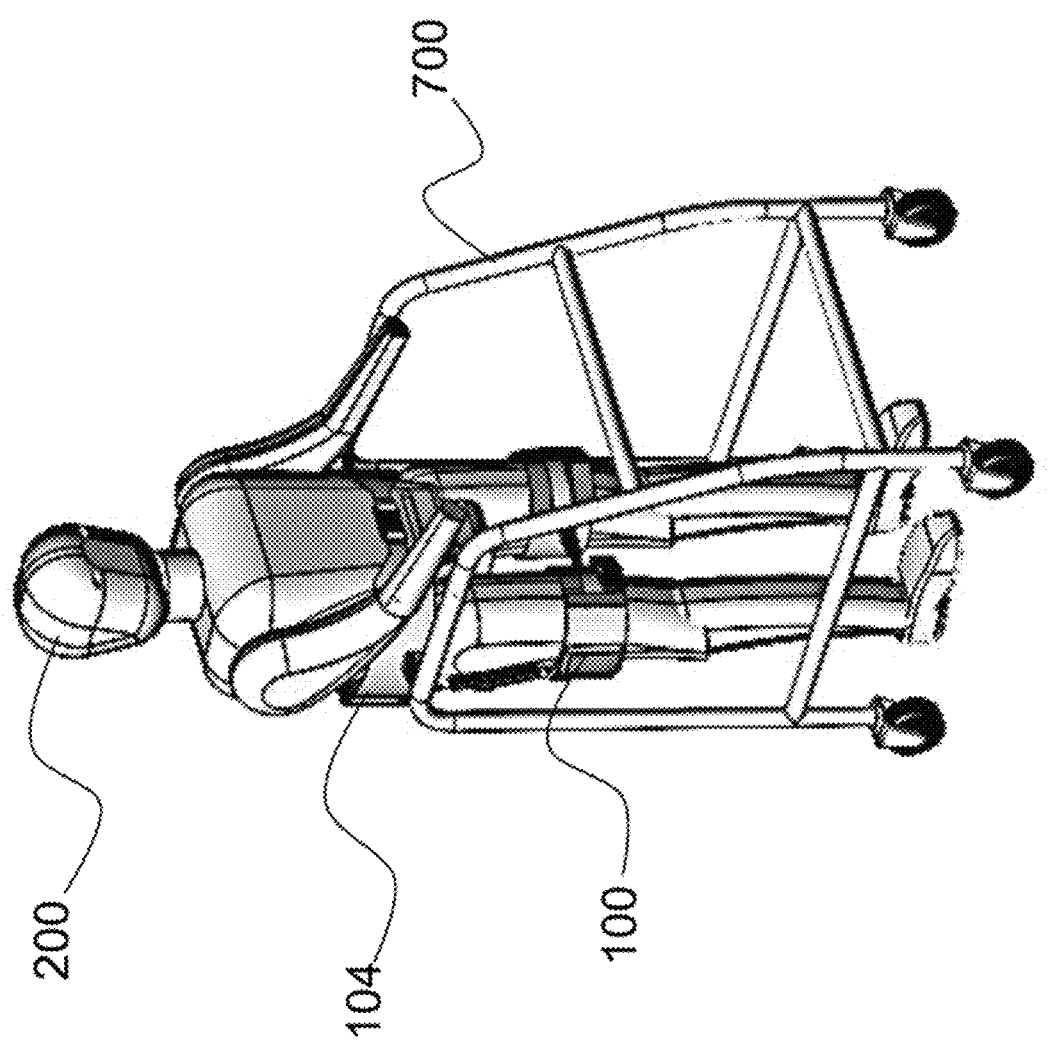
FIG. 7 is a front, perspective-view illustration of the transfer belt attached to a walker according to some embodiments of the present disclosure.
Figure 8:
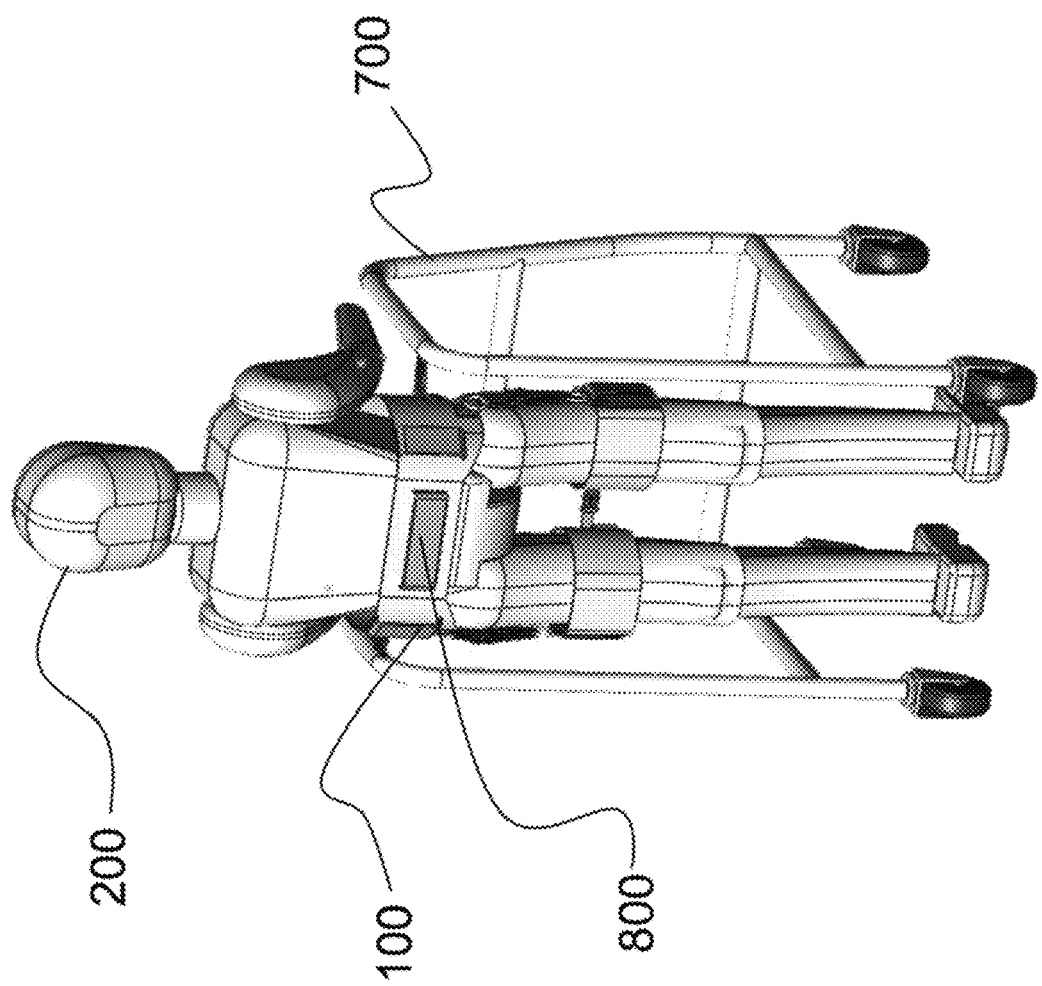
FIG. 8 is a rear, perspective-view illustration of the transfer belt with a person in a standing position according to some embodiments of the present disclosure.

FIG. 6 is a view of a person 200 utilizing the transfer belt 100 to be transferred with a mechanical lift 600. The mechanical lift straps 602 can connect around or to) the handles of the waist band and thigh bands via any suitable connection mechanism. FIG. 7 shows the person 200 wearing the transfer belt 100, which is attached to a walker 700 via its straps. For instance, the handles attached to the waist band 104 can be used for connection to the walker 700. The handles may include a hook closure (similar to a carabiner), a Velcro closure, or any other suitable mechanism that provides a secure, but detachable connection. As can be appreciated by one skilled in the art, the transfer belt worn by the individual can also be attached to a gait trainer, stander, or other assistance device. FIG. 8 illustrates a rear representation of the transfer belt 100 with a person 200 in a standing, position at a walker 700. A horizontal rear waist handle 800 across the back of the transfer belt 100 allows for additional manual support by a caregiver 502 when the person 200 wearing the transfer belt 100 is ambulating, as shown in FIG. 9.

FIG. 10 depicts personnel (e.g., caregivers 502, nurse) transferring a person 200 using a right side-left side technique holding the transfer belt 100. Another possible transfer (not shown) would be a top-bottom technique with one caregiver using two handles on the waist band with another caregiver holding the handles on each individual thigh band.

Figure 11:
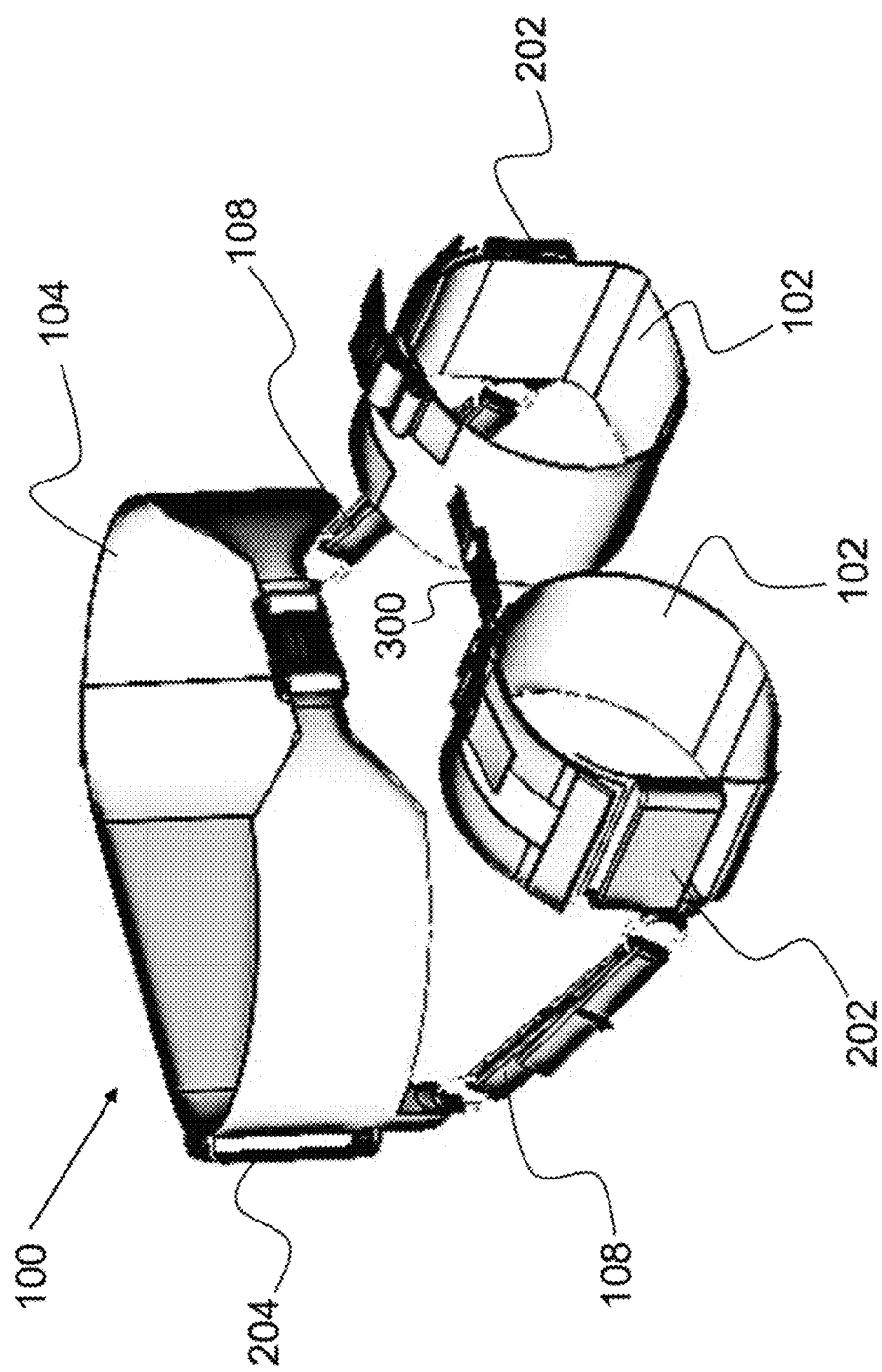
FIG. 11 is a front, perspective-view illustration of the transfer belt and components according to some embodiments of the present disclosure.
Figure 12:
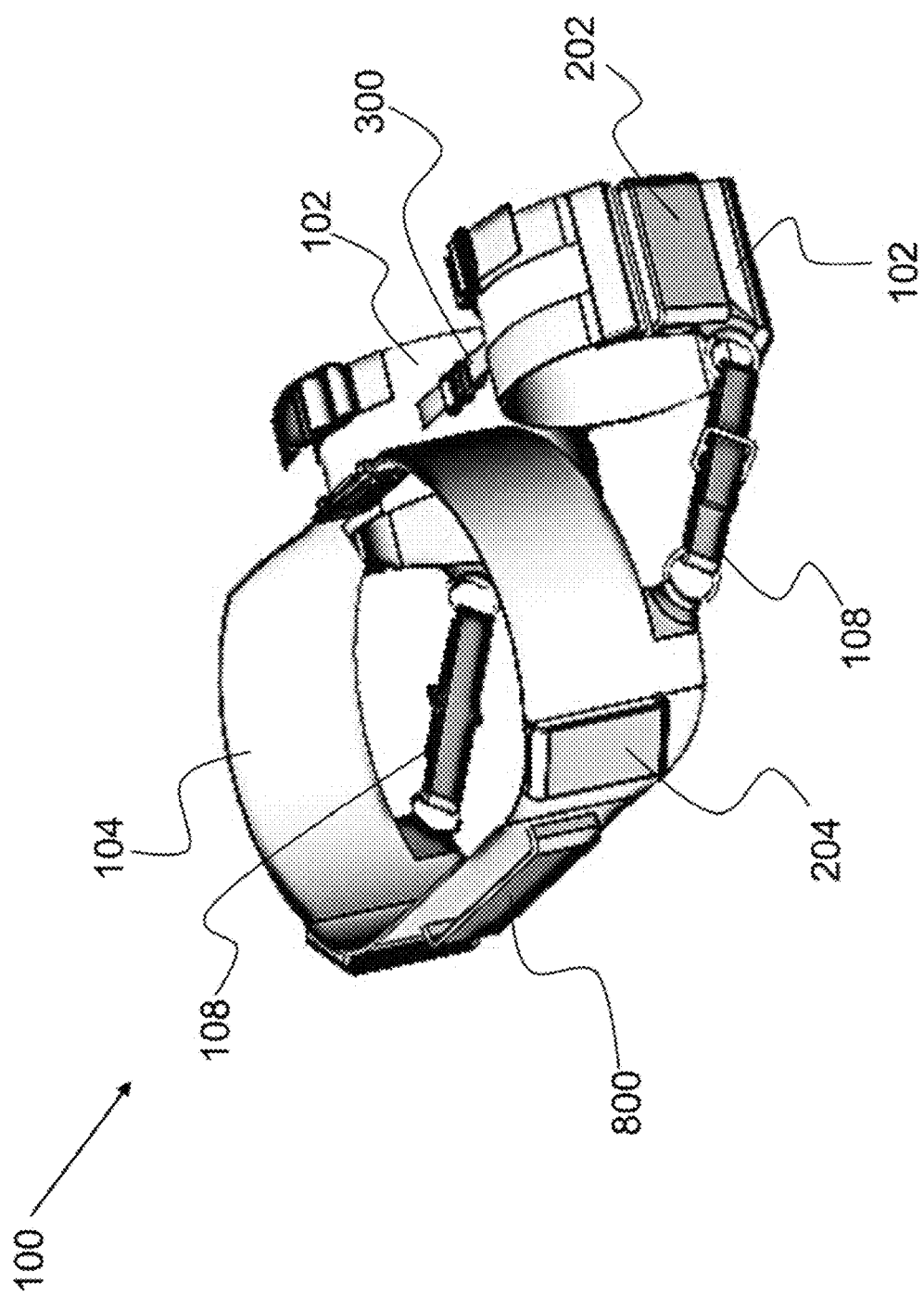
FIG. 12 is a side, perspective-view illustration of the transfer belt and components according to some embodiments of the present disclosure.
Figure 13:
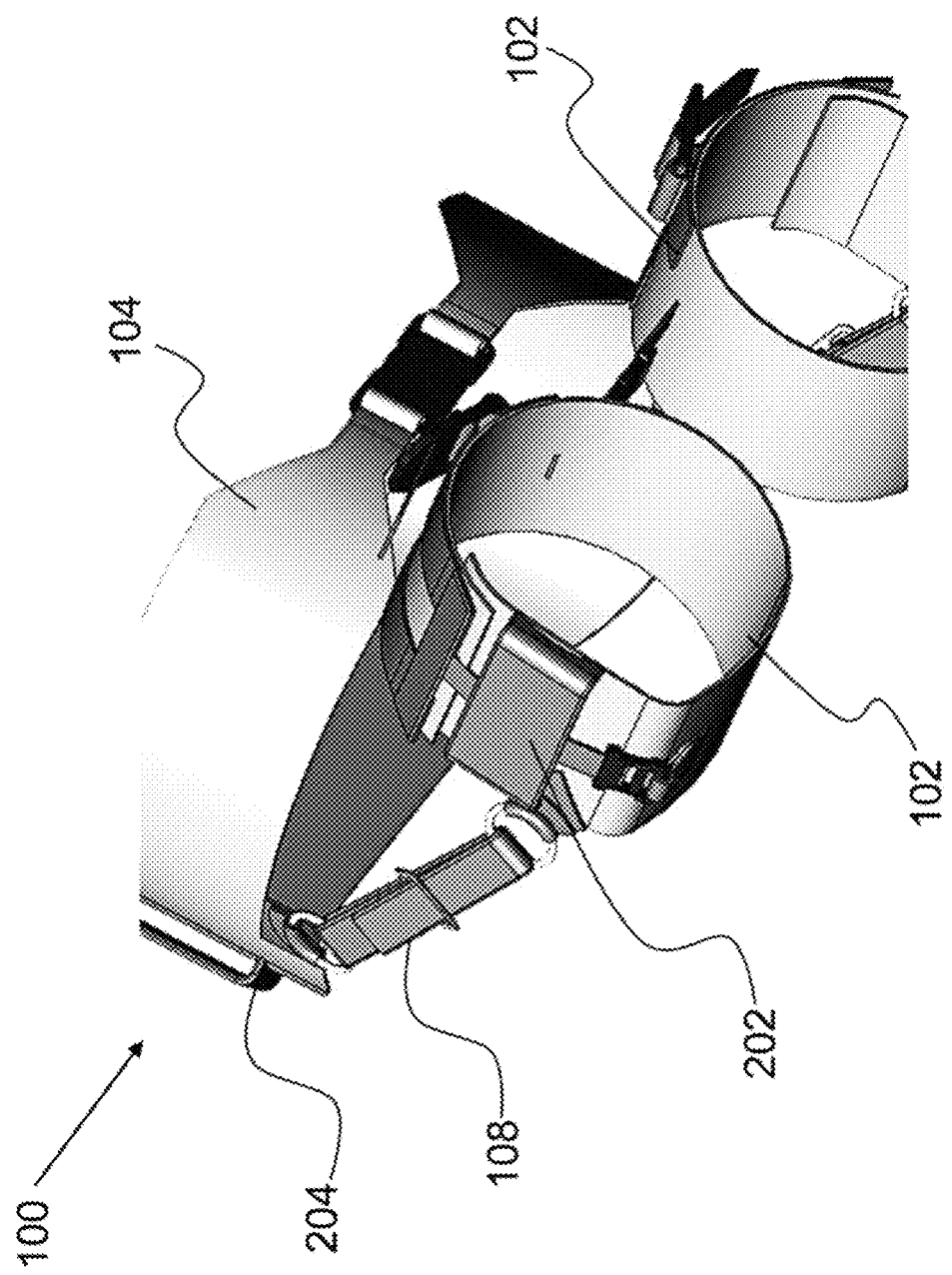
FIG. 13 is a bottom, perspective-view illustration of the transfer belt according to some embodiments of the present disclosure.

FIG. 11 is a depiction of the multiple components of the transfer belt 100. Shown are the waist band 104 with an adjustable length strap and lift handles 204, thigh bands 102 with adjustable length interlocking handles 202, an interconnect straps 108, which join the waist band 104 to the thigh bands 102, and an adjustable thigh strap connection strap 300 which joins the thigh bands 102 between the legs. The waist band 104 and thigh bands 102 may be interconnected via adjustable nylon straps and a buckle (or any other suitable mechanism that provides a stable connection). FIG. 12 illustrates an additional view of the transfer belt 100 and components including those listed above, plus a horizontal rear lift handle 800 along the back of the waist band 104. Further, FIG. 13 depicts another view of the transfer belt 100 and components.

Figure 14:
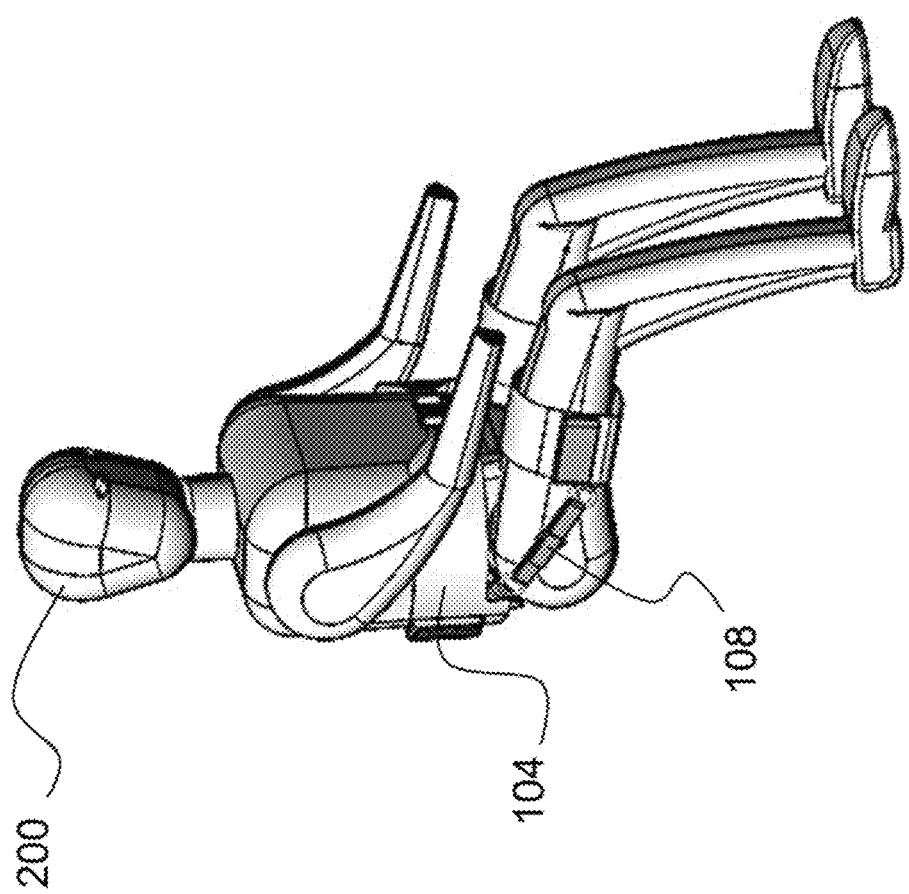
FIG. 14 is front, perspective-view illustration of a person sitting while wearing the transfer belt according to some embodiments of the present disclosure.
Figure 15:
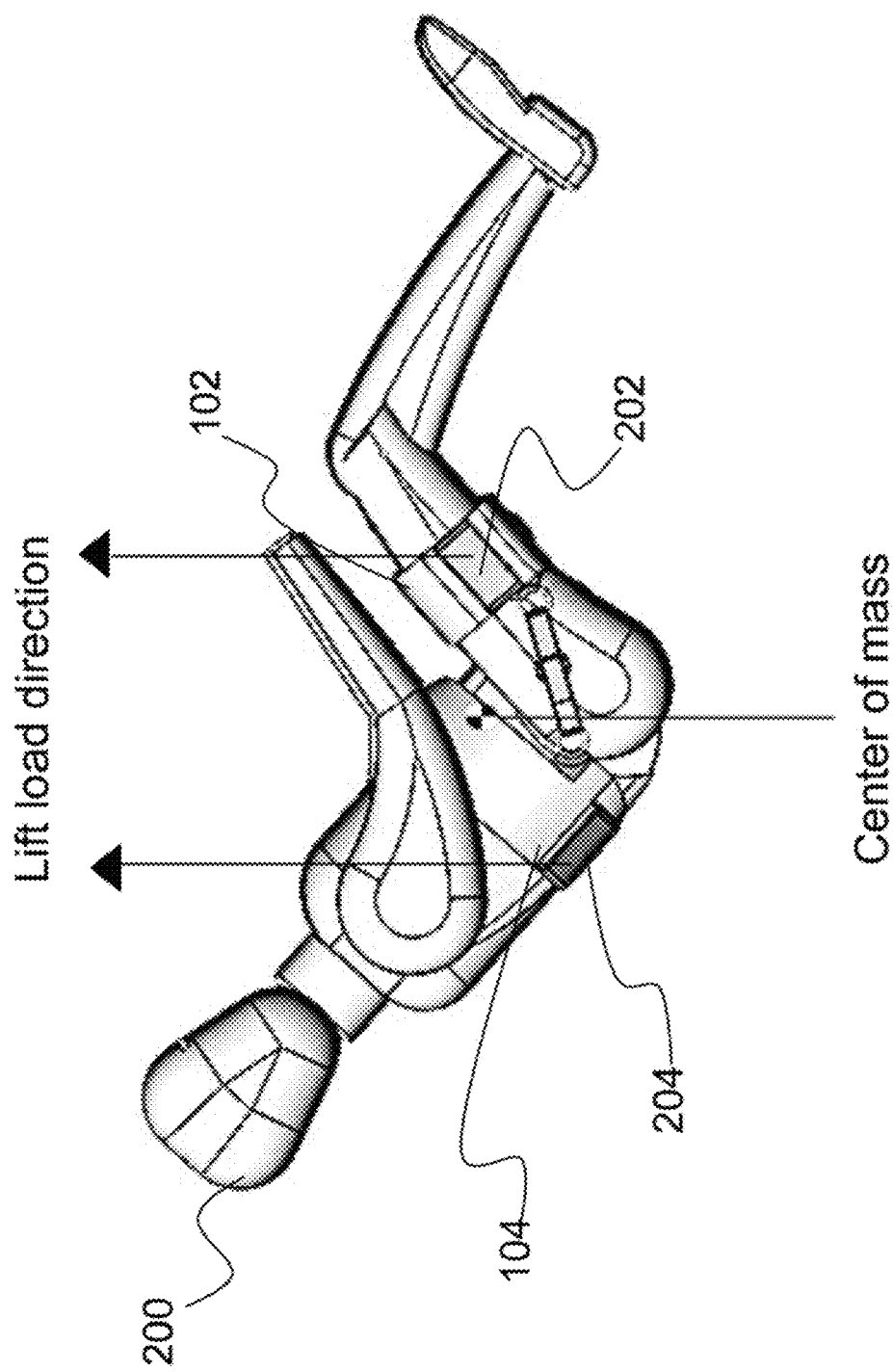
FIG. 15 is side-view illustration of a person positioned as he would be during a transfer with forces and lift directions shown according to some embodiments of the present disclosure.

FIG. 14 is front, perspective-view illustration of a person 200 sitting while wearing the transfer belt. From this view, the interconnect straps 108 can be seen positioned extending from the waist band 104 along a hip area of the person 200. FIG. 15 depicts a person 200 wearing the transfer belt 100 positioned as he would be during a transfer with forces and lift directions shown according to some embodiments of the present disclosure.

The waist band 104 comprises a horizontal strap designed to wrap around the person's waist between the hips and armpits. It is constructed of an easily cleaned and sanitized, waterproof or water resistant material that is flexible enough to easily bend and wrap around the patient. Nylon, polyester, or other suitable materials may be used. The waist band 104 connects on the front of the patient via, for instance, a male and a female buckle on each side of the waist band 104. As can be appreciated by one skilled in the art, other forms of connection can be utilized provided that they provide a strong connection. Adjustable nylon straps ensure a secure fit. Furthermore, the transfer belt can comprise slight padding (or a neoprene configuration) to reduce any discomfort for the patient. Additionally, two lateral handles (204) are present, along with a horizontal handle along the back (800) for caregiver control.

The thigh bands 102 wrap around the patient's thighs between the hips and the knees. The thigh bands 102 are made of an easily cleaned and sanitized, waterproof or water resistant material that is flexible enough to easily bend and wrap around the leg. Nylon, polyester, or other similar materials may be used. The band may utilize industrial strength hook-and-loop fasteners (Velcro) or another suitable material to secure firmly around the leg. An adjustable handle (202) on the overlying thigh band 102 may also be used to ensure safety and security of the strap.

Figure 16:
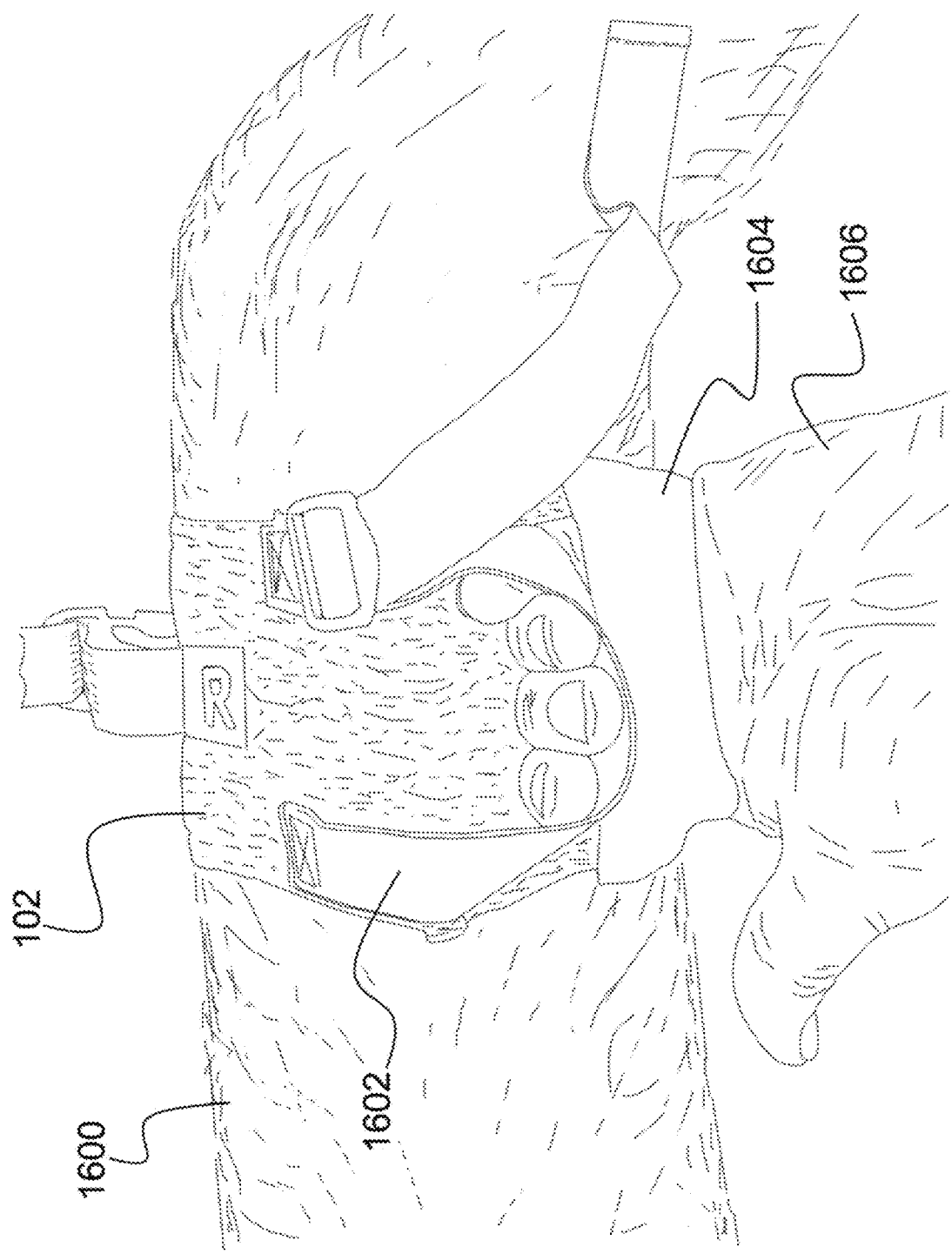
FIG. 16 is an illustration of interlocking handles according to some embodiments of the present disclosure.

FIG. 16 is an illustration of a thigh band 102 worn around the thigh 1600 of a person patient, depicting the set of interlocking handles. As shown in FIG. 16, the set of interlocking handles comprises an adjustable overlying handle 1602 and an underlying handle 1604 to ensure safety and security of the hand 1606 bold of the caretaker. The adjustable overlying handle 1602 overlays the underlying handle 1604 to allow a secure grip around both handles at the same time. Additionally, a handle 202 is present on the anterior lateral aspect of the thigh band, when positioned correctly. A buckle with an adjustable connection strap 300 can also be used to connect the right and left thigh hands 102 together for additional security.

Significantly, the transfer belt 100 distributes the center of mass between the waist band 104 and thigh band handles 202. This can be seen in FIG. 15. This is a consideration that has not been made, or met by the prior art. The invention described herein allows for a stable and safe inclined carry, as shown in FIG. 15. The advantage of this feature is that the patient will be transferred with the best possible stability and will, therefore, be safer during the transfer. It is also safer for the caretakers, because they will not have to deal with sudden changes in stability and are, therefore, much less likely to have a misstep that could cause them to drop the patient, causing irreparable harm to the patient. In other words, the described invention, provides improved rotational inertia (or resistance to rotational change) due to its center of mass feature and leveraged straps. This is a significant distinction from the prior art transfer systems which carry the weight of the patient in an off-center of mass fashion, thereby increasing the tendency to rotate. For instance, one existing harness has a single strap that wraps around both legs. In this configuration, a stronger caregiver holding one side of the patient's legs via the single strap could cause the strap to slide to one side based on caretaker force input, which would cause a transfer of weight to the weaker caregiver on the other side of the patient. This would not only cause distress to the weaker caregiver, but could result in dropping the patient. A sling-type harness wrapped around both thighs could slide side-to-side based on caretaker force input, making the person 200 unstable and uncomfortable. If the person 200 leans or tips forward, the sling-type harness will act as a fulcrum point and accelerate the forward moment of rotation of person 200, thereby crossing the caretakers' hands and causing loss of control and potential harm to the person 200 and both caretakers. Thus, the transfer belt 100 described herein has many advantages in properly supporting both patient 200 and caretakers.

Another major advantage of the transfer belt 100 is that it does not require a caregiver to lift the patient at all to slide it underneath the patient to fasten it. In fact, if the "seat depth" of the wheelchair or other seat is shallow enough, the thigh bands 102 can be placed on without having to move or lift the leg at all. Even if the seat is "deep", the individual thigh bands 102 can be easily put on by lifting one kg at a time to get under the bottom, and not the entire body. This is an advantage above anything that crosses underneath the bottom, since any patient already sitting would need to be either lifted or otherwise maneuvered to fit such other devices.

Other modifications and variations may readily occur to those skilled in the art upon reading the present disclosure or seeing the invention in practice. It is intended that all such modifications and variations are included within the scope of the invention, which is limited only by the appended claims and equivalents thereof.

What is claimed is:

1. A transfer belt for assisting in transporting an individual, comprising:
   a waist band for securing around the waist of the individual;
   a pair of thigh bands, each thigh band configured to be secured around a single thigh of the individual,
   wherein each thigh band comprises an adjustment buckle and strap, such that each thigh band is configured to be independently secured around the single thigh of the individual;
   a pair of interconnecting straps, each interconnecting strap connecting a thigh band with the waist band, such that when the transfer belt is worn by the individual, one of the pair of interconnecting straps is positioned between the waist band and one of the pair of thigh bands along a first hip area of the individual, and the other of the pair of straps is positioned between the waist band and the other of the pair of thigh bands along a second hip area of the individual; and
   an adjustable bridge strap for connecting the pair of thigh bands to one another between the thighs of the individual such that the individual can be supported in a standing position.

2. The transfer belt as set forth in claim 1, further comprising at least one waist handle connected with the waist band for assisting in lifting the individual.

3. The transfer belt as set forth in claim 2, further comprising at least one thigh handle connected with each of the pair of thigh bands for assisting in lifting the individual.

4. The transfer belt as set forth in claim 3, wherein the at least one waist handle and the at least one thigh handle are formed to be connectable with a mechanical lift.

5. The transfer belt as set forth in claim 2, wherein the at least one waist handle is formed to be connectable with a walking assistance device.

6. The transfer belt as set forth in claim 1, further comprising a pair of removable supporting shoulder straps formed to be connectable with at least one of a waist handle and a thigh handle, wherein each removable supporting shoulder strap is wearble by a caretaker for transporting the individual.

7. The transfer belt as set forth in claim 6, wherein a connecting strap connects the pair of removable supporting shoulder straps, such that if the pair of shoulder straps are worn by the caregivers, the connecting strap is positioned at an upper back of the individual to provide additional support to an upper torso and head of the individual.

8. The transfer belt as set forth in claim 1, wherein each of the pair of interconnecting straps is adjustable.

9. The transfer belt as set forth in claim 1, wherein the individual wearing the transfer belt can be transferred to and from a seated position, a standing position, or a lying position without adjustments to the transfer belt.

10. The transfer belt as set forth in claim 1, wherein each thigh band comprises a set of interlocking handles.

11. The transfer belt as set forth in claim 1, wherein the adjustable bridge strap comprises an adjustable buckle and strap.

12. A method for forming a transfer belt for assisting in transporting an individual, the method comprising acts of:
    forming a waist band for securing around the waist of the individual;
    forming a pair of thigh bands, each thigh band formed to be secured around a single thigh of the individual,
    wherein each thigh band is formed with an adjustment buckle and strap, such that each thigh band is formed to be independently secured around the single thigh of the individual;
    forming a pair of interconnecting straps, each interconnecting strap formed to connect a single thigh band with the waist band, such that when the transfer belt is worn by the individual, one of the pair of interconnecting straps is positioned between the waist band and one of the pair of thigh bands along a first hip area of the individual, and the other of the pair of straps is positioned between the waist band and the other of the pair of thigh bands along a second hip area of the individual; and
    forming an adjustable bridge strap for connecting the pair of thigh bands to one another between the thighs of the individual such that the individual can be supported in a standing position.

13. The method as set forth in claim 12, further comprising an act of forming a pair of removable supporting shoulder straps connectable with at least one of a waist handle and a thigh handle, wherein each removable supporting shoulder strap is wearable by a caretaker for transporting the individual.

14. The method as set forth in claim 13, further comprising an act of forming a connecting strap connecting the pair of removable supporting shoulder straps, such that if the pair of shoulder straps are worn by the caregivers, the connecting strap is positioned at an upper back of the individual to provide additional support to an upper torso and head of the individual.

15. The method as set forth in claim 12, further comprising an act of forming at least one thigh handle connected with each of the pair of thigh bands for assisting in lifting the individual.

16. The method as set forth in claim 12, further comprising an act of forming a set of interlocking handles connected with each thigh band.

17. The method as set forth in claim 12, further comprising an act of forming the adjustable bridge strap to have an adjustable buckle and strap.

\* \* \* \* \*